United States Patent [19]

Manzouji et al.

[11] Patent Number: 5,874,602

[45] Date of Patent: Feb. 23, 1999

[54] PROCESS FOR THE PREPARATION OF RADICALLY POLYMERIZABLE GROUP-FUNCTIONAL SILANOL COMPOUNDS

[75] Inventors: Ryuko Manzouji; Tadashi Okawa, both of Chiba Prefecture, Japan

[73] Assignee: Dow Corning Toray Silicone Co., Ltd., Tokyo, Japan

[21] Appl. No.: 49,366

[22] Filed: Mar. 27, 1998

[30] Foreign Application Priority Data

Mar. 28, 1997 [JP] Japan .................................. 9-094878

[51] Int. Cl.$^6$ ...................................................... C07F 7/08
[52] U.S. Cl. ........................... 556/463; 556/457; 556/440
[58] Field of Search ................... 556/463, 437, 556/440

[56] References Cited

U.S. PATENT DOCUMENTS

| | | | |
|---|---|---|---|
| 3,328,448 | 6/1967 | Barnes et al. | 556/463 |
| 3,542,837 | 11/1970 | Swihart | 556/463 |
| 4,207,247 | 6/1980 | Knollmueller | 556/463 |
| 4,845,259 | 7/1989 | Arai et al. | 556/440 |
| 5,488,125 | 1/1996 | Omura et al. | 556/463 |

FOREIGN PATENT DOCUMENTS 6-256355  9/1994  Japan .

*Primary Examiner*—Paul F. Shaver
*Attorney, Agent, or Firm*—Alex Weitz

[57] ABSTRACT

A process for preparing a compound having the formula $$\begin{array}{c} R^1 \\ | \\ X-Si-OH \\ | \\ R^1 \end{array}$$

is disclosed, said process comprising hydrolyzing an organosilicon compound of the formula $$\begin{array}{c} R^1 \\ | \\ (X-Si)_m-N-R^2{}_{3-m} \\ | \\ R^1 \end{array}$$

wherein X is a radically polymerizable group-functional organic group, $R^1$ is independently selected from monovalent hydrocarbon groups that are free of aliphatic unsaturation, $R^2$ is independently selected from the group consisting of hydrogen and a monovalent hydrocarbon group and m is an integer having a value of 1 to 3.

8 Claims, No Drawings

PROCESS FOR THE PREPARATION OF RADICALLY POLYMERIZABLE GROUP-FUNCTIONAL SILANOL COMPOUNDS

FIELD OF THE INVENTION

This invention relates to processes for the preparation of radically polymerizable group-functional silanol compounds. More particularly, the invention relates to a process for the preparation of radically polymerizable group-functional silanol compounds that exhibit excellent storage stability.

BACKGROUND OF THE INVENTION

Silanol compounds containing a radically polymerizable group such as the methacryloxy group are useful for potting electrical and electronic components. Japanese Patent Application Laid Open (Kokai or Unexamined) Number Hei 6-256355 (256,355/1994), for example, teaches the direct hydrolysis of 3-methacryloxypropyldimethylchlorosilane as one method for the preparation of such silanol compounds. Unfortunately, the implementation of this process on an industrial scale is highly problematic due to the use of highly flammable ether as solvent and use of column chromatography for purification of the obtained silanol compound. In addition, in the absence of purification by column chromatography, the silanol compound afforded by this process suffers from a decline in purity with elapsed time and results in a poor storage stability. Japanese Patent Publication (Kokoku) Number Hei 3-49910 (49,910/1991) teaches a process for synthesizing silanol compounds by first reacting chloropropyldimethylchlorosilane and potassium methacrylate and then hydrolyzing the product. However, the first-stage reaction in this process must be run for an extended period of time at high temperatures. This results in polymerization of the methacryloxy group during the synthesis, which prevents production of the desired silanol compound.

SUMMARY OF THE INVENTION

The object of the present invention is to provide a highly productive process for the preparation of radically polymerizable group-functional silanol compounds that are very pure, do not suffer from a decline in purity with elapsed time, and exhibit an excellent storage stability.

The present invention, therefore, relates to a process for the preparation of radically polymerizable group-functional silanol compounds of the formula

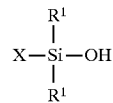

wherein X represents a radically polymerizable group-functional organic group and $R^1$ is independently selected from monovalent hydrocarbon groups that are free of aliphatic unsaturation, said process being characterized by hydrolyzing an organosilicon compound of the formula

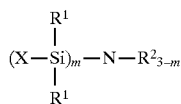

wherein X and $R^1$ are defined as above, $R^2$ is a hydrogen atom or the same or different monovalent hydrocarbon group, and m is an integer from 1 to 3.

The present invention has been disclosed in Japanese Patent Application Number Hei 09/094878, the full disclosure of which is hereby incorporated by reference.

DETAILED DESCRIPTION OF THE INVENTION

The present invention employs an organosilicon compound, having the following general formula.

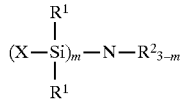

The radically polymerizable group-functional organic group X in this organosilicon compound can be exemplified by methacryloxy-functional organic groups, methacryl-functional organic groups, and the 4-vinylphenyl group. Preferred among these are groups expressed by the formula

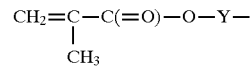

in which Y is a divalent hydrocarbon group having at least 2 carbon atoms or the group $—R^3—O—R^3—$ in which $R^3$ is independently selected from divalent hydrocarbon groups. The divalent hydrocarbon groups Y and $R^3$ are exemplified by ethylene, propylene, butylene, and hexylene. The group $—R—O—R^3—$ is exemplified by ethyleneoxypropylene. Each $R^1$ is independently selected from monovalent hydrocarbon groups that are free of aliphatic unsaturation, and $R^2$ is a hydrogen atom or the same or different monovalent hydrocarbon group. The monovalent hydrocarbon groups encompassed by $R^1$ and $R^2$ are exemplified by alkyl groups having 1 to 18 carbon atoms, such as methyl, ethyl, and the like; aryl groups such as phenyl, tolyl, xylyl, and the like; and aralkyl groups such as phenethyl, diphenylmethyl, and the like. The subscript m is an integer having a value of 1 to 3 inclusive.

The above described organosilicon compound can be exemplified by compounds having the following formulas.

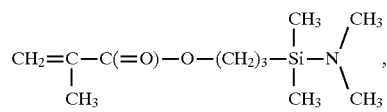

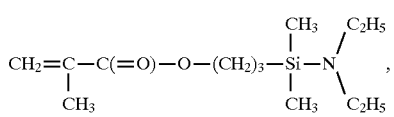

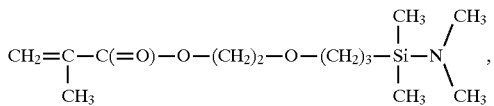

3

-continued $$(CH_2=C(CH_3)-C(=O)-O-(CH_2)_3-Si(CH_3)_2)_2-NH,$$

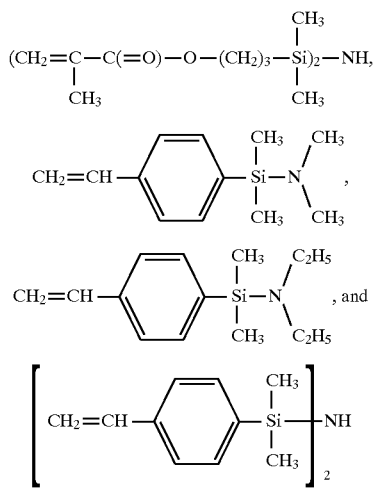

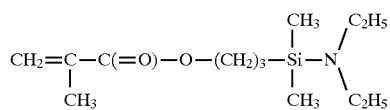

The above organosilicon compound can be synthesized by heretofore known processes. For example, the organosilicon compound can be synthesized by a reaction in which methacryloxypropyldimethylchlorosilane $CH_2=C(CH_3)COO(CH_2)_3Si(CH_3)_2Cl$ is added dropwise to toluene solvent containing diethylamine in an amount at least twice that of the silane on a molar basis. Distillation of the reaction mixture afforded by this process is preferably carried out in the presence of a suitable polymerization inhibitor. The known polymerization inhibitors which can be used for this purpose, include 2,6-di-tert-butyl-4-methylphenol, hydroquinone, hydroquinone monomethyl ether, phenothiazine, and the like.

The preparative process according to the present invention is characterized by the addition of water to, and the execution of an hydrolysis reaction on the above-described organosilicon compound (i.e., hydrolyzing the organosilicon compound). An amount of water sufficient for the hydrolysis reaction of the organosilicon compound should be added, but the quantity of water used for the reaction is not otherwise critical. However, water is preferably added in an amount at least equimolar with the organosilicon compound. Specifically, the ratio moles organosilicon compound: moles water is preferably in the range from 1:1 to 1:100 and more preferably is in the range from 1:2 to 1:10. This hydrolysis reaction can be run at room temperature and is particularly preferably run in the range from 0° to 30° C. in order to avoid the rise in temperature caused by the heat of reaction. The hydrolysis reaction under consideration can be run in the presence of generally known hydrolysis catalysts, but it can also be run in the absence of such catalysts. The progress of the reaction can be monitored by analyzing the reaction solvent by gas chromatography (GLC), and the reaction is considered complete when the peak for the starting organosilicon compound has disappeared. After completion of the reaction, it will generally be necessary to remove the amine or ammonia by-product with a water wash, and it is preferable at this point to have preliminarily neutralized the amine or ammonia by-product using acetic acid or the like. The water wash is generally followed by azeotropic drying

4 using a suitable solvent. The solvent used in azeotropic drying is preferably an aliphatic hydrocarbon solvent such as hexane in order to operate at a low reflux temperature and thereby inhibit silanol group condensation. After azeotropic drying, the low boilers, e.g., the solvent and so forth, are removed, for example, by distillation at reduced pressure. The desired radically polymerizable group-functional silanol compound can then be recovered by distillative purification.

As has been described hereinabove, the process according to the present invention for the preparation of radically polymerizable group-functional silanol compounds does not involve the direct hydrolysis of halogen-functional organosilicon compounds, but rather involves the hydrolysis of nitrogenous organosilicon compounds. As a consequence, the process according to the present invention offers the advantage of producing high-purity radically polymerizable group-functional silanol compounds whose purity does not deteriorate with elapsed time and which, as a result, exhibit an excellent storage stability. Moreover, since the preparative process according to the present invention does not require the use of highly flammable ether or purification by column chromatography, it supports and enables industrial utilization and large-scale production. The preparative process according to the present invention as described above is particularly well suited for the production of methacryloxyfunctional silanol compounds which are useful in electrical potting applications and as intermediates for the preparation of curable acrylate polymers.

EXAMPLES

The invention is explained below in greater detail through a working example.

Reference Example 1

While operating under a nitrogen atmosphere, 700 g of toluene and 400 g (5.48 mol) of diethylamine were introduced into a 5-liter flask equipped with a stirrer, thermometer, condenser, and addition funnel. 500 g (2.27 mol) of methacryloxypropyldimethylchlorosilane was then added dropwise while cooling on an ice-water bath in such a manner that the reaction temperature did not exceed 30° C. After the completion of addition, stirring was continued for an additional 1 hour, after which it was confirmed that the pH of the reaction solution was not acidic and also by GLC that none of the starting methacryloxypropyldimethylchlorosilane remained. The salt by-product was then removed by filtering the reaction mixture through a glass filter. One half gram of 3,5-di-tert-butyl-4-hydroxybenzyldimethylammonium chloride and 0.05 g of 2,6-di-tert-butyl-4-methylphenol were added to the obtained filtrate and, after the low boilers had been removed by heating, distillation under reduced pressure yielded a 422.6 g fraction at 107°–110° C./1.5 mmHg. Analysis of the obtained fraction by nuclear magnetic resonance (NMR) confirmed it to be an organosilicon compound having the following formula and having a purity (by GLC) of 99%.

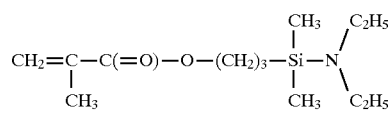

Example 1

While operating under a nitrogen atmosphere, 300 g (1.48 mol) of the organosilicon compound prepared in Reference Example 1, 50 g of water, and 50 g of ice were introduced into a 1-liter flask equipped with a stirrer, thermometer, and condenser and were stirred for one hour. Analysis of the reaction solution at this point by GLC showed that the peak for the starting organosilicon compound had disappeared, which indicated that the reaction was complete. The flask was then brought to quiescence, the aqueous layer was separated off, and the reaction solution was made weakly basic by the addition of acetic acid in a quantity slightly less than that required for neutralization. 300 g hexane was added and the resulting organic layer was washed twice with water. 0.6 g of 2,6-di-tert-butyl-4-methylphenol was then added to the organic layer followed by azeotropic drying for one hour. Subsequent to azeotropic drying the hexane was distilled from the reaction mixture by heating under reduced pressure, after which 210 g of a fraction at 100° to 110° C./0.5 mmHg was recovered. NMR analysis of this fraction confirmed it to be the methacryloxypropyl-functional silanol compound of the formula given below and having a purity of 99% by GLC.

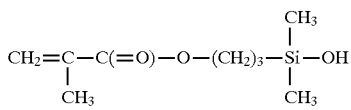

This methacryloxypropyl-functional silanol compound was placed in a polyethylene container and held for 14 days at room temperature in order to measure changes in its purity. Purity was determined by GLC analysis of the silanol compound, the results being reported in Table 1.

Comparative Example 1

500 g of water, 30.9 g (367.3 mmol) of sodium bicarbonate, and 200 ML of ether were introduced into a 2-liter flask equipped with a stirrer, thermometer, and addition funnel. Then, a mixture of 50 g (226.8 mmol) of methacryloxypropyldimethylchlorosilane and 50 mL of ether was added dropwise while cooling on a salted ice-water bath so as to prevent the reaction temperature from exceeding 0° C. After the completion of addition the reaction was stirred for an additional one hour. After confirming that the pH of the reaction solution was not acidic, the flask was brought to quiescence, the aqueous layer was separated off, and the organic layer was washed with water 3 times. 20 g of anhydrous sodium sulfate was added to the organic layer, and, after standing for one hour, the organic layer was filtered through a glass filter. 0.0025 g of 4-methoxyphenol was added to the recovered organic layer and the low boilers were then removed by heating at a temperature not exceeding 30° C. Analysis of the residue by NMR confirmed it to be a methacryloxypropyl-functional silanol compound having the formula shown below and having a purity of 99% by GLC.

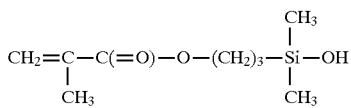

When the residue obtained as described above was directly distilled under reduced pressure, a condensation reaction occurred within several hours after distillation and the purity by GLC was reduced. The change in the purity of this methacryloxypropyl-functional silanol compound was followed as a function of time as in Example 1. These results are also reported in Table 1.

TABLE 1

| | number of days of storage: | | | |
|---|---|---|---|---|
| | 0 | 1 day | 3 days | 14 days |
| Example 1 | 99% | 99% | 99% | 99% |
| Comparative Example 1 | 99% | 89% | 61% | 40% |

The values are the purity by GLC analysis.

That which is claimed is:

1. A process for preparing a compound having the formula

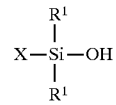

said process comprising hydrolyzing an organosilicon compound of the formula

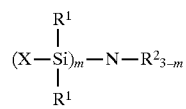

wherein X is a radically polymerizable group-functional organic group, $R^1$ is independently selected from monovalent hydrocarbon groups that are free of aliphatic unsaturation, $R^2$ is independently selected from the group consisting of hydrogen and a monovalent hydrocarbon group and m is an integer having a value of 1 to 3.

2. The process according to claim 1, wherein $R^1$ and $R^2$ are independently selected from the group consisting of alkyl groups having 1 to 18 carbon atoms, aryl groups and aralkyl groups.

3. The process according to claim 2, wherein $R^1$ and $R^2$ are independently selected from the group consisting of methyl, ethyl and phenyl.

4. The process according to claim 1, wherein X is selected from the group consisting of methacryloxy-functional organic groups, methacryl-functional organic groups and 4-vinylphenyl group.

5. The process according to claim 4, wherein X is represented by the formula

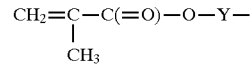

in which Y is a divalent group selected from the group consisting of a hydrocarbon group having at least 2 carbon atoms and a group having the formula

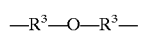

in which $R^3$ is independently selected from divalent hydrocarbon groups.

6. The process according to claim 5, wherein Y and $R^3$ are selected from the group consisting of ethylene, propylene, butylene and hexylene.

7. The process according to claim 6, wherein $R^1$ and $R^2$ are independently selected from the group consisting of methyl, ethyl and phenyl.

8. The process according to claim 1, wherein said organosilicon compound has a formula selected from the group consisting of

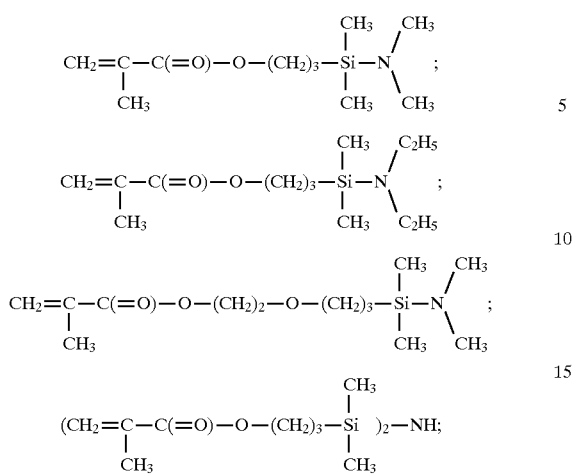
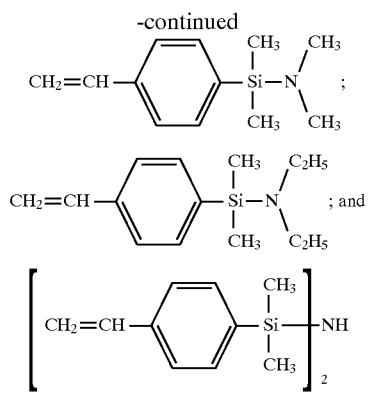
* * * * *